United States Patent [19]

Mülleder et al.

[11] Patent Number: 5,602,247

[45] Date of Patent: Feb. 11, 1997

[54] PROCESS FOR THE PURIFICATION OF AQUEOUS SOLUTIONS OF TERTIARY AMINE-OXIDES

[75] Inventors: Eduard Mülleder, Linz; Heinrich Firgo, Vöcklabruck, both of Austria

[73] Assignee: Lenzing Aktiengesellschaft, Austria

[21] Appl. No.: 454,315

[22] PCT Filed: Feb. 1, 1995

[86] PCT No.: PCT/AT95/00022

§ 371 Date: Aug. 14, 1995

§ 102(e) Date: Aug. 14, 1995

[87] PCT Pub. No.: WO95/23885

PCT Pub. Date: Sep. 8, 1995

[30] Foreign Application Priority Data

Mar. 1, 1994 [AT] Austria ................................ A 430/94

[51] Int. Cl.⁶ ............................. D01F 13/02; B01J 39/22; B01J 41/16
[52] U.S. Cl. ........................... 536/57; 210/670; 210/681; 210/683
[58] Field of Search ........................... 536/57; 210/670, 210/681, 683

[56] References Cited

U.S. PATENT DOCUMENTS

| | | | |
|---|---|---|---|
| 4,577,013 | 3/1986 | Merz | 536/43 |
| 4,724,207 | 2/1988 | Hou et al. | 435/180 |
| 5,053,138 | 10/1991 | Korger et al. | 210/670 |
| 5,157,055 | 10/1992 | Akagi et al. | 521/25 |
| 5,409,532 | 4/1995 | Astegger et al. | 106/163.1 |
| 5,441,689 | 8/1995 | Laity | 264/179 |

FOREIGN PATENT DOCUMENTS

| | | |
|---|---|---|
| 356419 | 8/1989 | European Pat. Off. . |
| 427701 | 5/1991 | European Pat. Off. . |
| 553070 | 1/1993 | European Pat. Off. . |
| 254199 | 2/1988 | Germany . |
| 93-11287 | 6/1993 | WIPO . |

OTHER PUBLICATIONS

English language abstract of DD 254,199.
English language abstract of EP 356,419.
English language abstract of EP 427,701.
English language abstract of EP 553,070.
Rogowin und Galbraich, "Die chemische Behandlung und Modifizierung der Zellulose", Georg Thieme Verlag, p. 97–(1983).
Ullman, Encyclopedia of Industrial Chemistry, vol. A14, p. 396.

Primary Examiner—Nathan M. Nutter
Attorney, Agent, or Firm—Brumbaugh, Graves, Donohue & Raymond

[57] ABSTRACT

The invention is concerned with a process for the production of cellulose molded bodies. This process has the following steps:

(A) dissolving cellulose in an aqueous solution of a tertiary amine-oxide to produce a moldable cellulose solution, (B) molding said cellulose solution and conducting said molded cellulose solution into an aqueous precipitation bath, wherein the cellulose is precipitated, thus producing a molded body and a spent precipitation bath, and (C) purifying said spent precipitation bath by contacting said precipitation bath with an ion exchanger, thus producing a purified aqueous amine-oxide solution which, optionally after concentration, is re-used again in step (A) as a cellulose solvent. In this process, the ion exchanger comprises a cellulose carrier which has attached groups which are capable of exchanging ions.

11 Claims, No Drawings

PROCESS FOR THE PURIFICATION OF AQUEOUS SOLUTIONS OF TERTIARY AMINE-OXIDES

BACKGROUND OF THE INVENTION

The present invention relates generally to a process for the purification of aqueous solutions of tertiary amine-oxides.

The viscose process is presently widely used to produce cellulose molded bodies. For some decades, scientists have searched for a replacement process for the production of cellulose molded bodies. An interesting replacement process having reduced environmental impact has been discovered. In this method, cellulose is dissolved without derivatization in an organic solvent, and this solution is extruded to form molded bodies, e.g. fibers and films. Such extruded fibers have been given the generic name Lyocell by BISFA (The International Bureau for the Standardization of man made fibers). BISFA defines a mixture of an organic chemical substance and water as an organic solvent.

It has been shown that a mixture of a tertiary amine-oxide and water is particularly useful as an organic solvent for the production of cellulose molded bodies. N-methylmorpholine-N-oxide (NMMO) is typically used as the amine-oxide. Other suitable amine-oxides are described e.g. in EP-A 0 533 070. A method for the production of moldable cellulose solutions is known e.g. from EP-A-0 356 419.

In this process, cellulose is precipitated from a molded cellulose solution in an aqueous precipitation bath. During this process, amine-oxide builds up in the precipitation bath. To render this method economical it is of decisive importance to recover and reuse nearly all of the amine-oxide. Thus the amine-oxide process has the following 3 main steps:

(A) dissolving cellulose in an aqueous solution of a tertiary amine-oxide, preferably N-methylmorpholine-N-oxide (NMMO), to produce a moldable cellulose solution, (B) molding said cellulose solution and conducting said molded cellulose solution into an aqueous precipitation bath wherein the cellulose is precipitated, thus producing a molded body and a spent precipitation bath, (C) regenerating (i.e. purifying and concentrating) the spent precipitation bath, thus producing a regenerated aqueous amine-oxide solution which is reused in step (A) as a cellulose solvent.

During this process, amine-oxide and degradation products of cellulose and the amine-oxide build up in the precipitation bath. These products may be heavily colored. If the colored products are not removed from the precipitation bath, the quality of the produced molded bodies will be impaired. Metal traces may also build up in the precipitation bath, which reduces process safety.

There are some proposals in the literature for removing these degradation products before using the amine-oxide solution again in step (A). Specifically, DD-A 254 199 describes a known process for purifying aqueous solutions of NMMO, wherein the solution passes through anion exchangers. In the first step of this process, the anion exchanger contains an exchange resin comprising a styrene-divinylbenzene copolymerizate carrying tertiary amine-groups of the —$CH_2N(CH_3)_2$ type. In the second step of this process, quaternary ammonium groups of the —$CH_2N(CH_3)_3OH$ type act as functional groups. According to DD-A 254 199, NMMO solutions treated according to the process are dark at the beginning of the purification, brown to yellow after the first process step and bright yellow to transparent after the second process step.

A disadvantage of this process is that the treated solutions have a high pH value, which subsequently requires more complex purification. Additionally, this process does not remove alkali and alkali-earth cations from the solution. The metal ions, alkali metal ions and alkali-earth metal ions lead to undesired precipitations and incrustation, unwanted insoluble substances in the solution, and reduced process safety. Although it is possible to remove these salts by adding a precipitation agent and subsequently filtering or through the use of other separating agents, these operations are disadvantageous because they introduce additional chemicals or require additional processing.

EP-A-0 427 701 describes a second known process for purifying aqueous amine-oxide solutions. Specifically, EP-A-0 427 701 describes a process wherein the purification is carried out in a one-step process with an anion exchanger which exclusively has quaternary tetraalkyl ammonium functional groups according to the formulas —$CH_2N^+(CH_3)_3X^-$ or —$CH_2N^+(CH_3)_2(CH_2OH)X^-$, wherein $X^-$ represents the anion of an inorganic or organic acid. In this process, the anion exchanger is regenerated using an aqueous acidic solution. The anion $X^-$ is preferably derived from a volatile acid, in particular carbonic acid, formic acid or acetic acid. These acids are also disclosed to be useful for regenerating the anion exchanger.

International Patent Application W093/11287 discloses regenerating the strong basic anion exchanger styrene-divinylbenzene copolymefizate by first using an aqueous solution of a strong inorganic acid and then soda lye (i.e. in two steps). The regeneration has to be carried out in two steps because the anion exchanger is colored so heavily by the solution to be purified that merely regenerating with aqueous NaOH does not suffice to remove the resin's color and regenerate its capacity. It is therefore only possible to achieve these results by treating the anion exchange a second time with a strong inorganic acid. This two-step procedure uses more chemicals and requires using strongly irritative substances (e.g. hydrochloric acid). Additionally it can be deduced from Example 5 of this document that the capacity of the anion exchanger is reduced to half of its original value after 10 operation cycles even when this two-step regeneration process is employed.

This styrene-divinylbenzene copolymerizate which is widely used as carrier in ion exchanging systems, is also disadvantageous because it will not rot and is difficult to reuse. Therefore, this ion exchanging system must after a certain time interval be incinerated as hazardous waste.

Alternative carriers are described in general technical manuals (see e.g. "Encyclopedia of Industrial Chemistry" by Ullmann, Volume A 14, page 396). Examples of such materials include polyacryl materials, phenol-formaldehyde resins or polyalkylamine resins. These materials must also eventually be incinerated as hazardous waste and usually must be produced using toxic or polluting starting materials (e.g. phenol-formaldehyde resins).

SUMMARY OF THE INVENTION

It is an object of the present invention to provide ion exchangers for the amine-oxide process which are able to purify spent NNMO solutions, such as spent precipitation baths, while avoiding the disadvantages of the prior art (e.g., styrene-divinylbenzene copolymerates). Another object of the invention is to provide a material which may be completely separated from the colored substances attached to it in a single step process.

The process according to the invention for the production of cellulose molded bodies comprises the following steps:

(A) dissolving cellulose in an aqueous solution of a tertiary amine-oxide, preferably N-methylmorpholine-N-oxide (NMMO), to produce a moldable cellulose solution, (B) molding said cellulose solution and conducting said molded cellulose solution into an aqueous precipitation bath wherein the cellulose is precipitated, thus producing a molded body and a spent precipitation bath, (C) purifying said spent precipitation bath by contacting said precipitation bath with an ion exchanger, thus producing a purified aqueous amine-oxide solution which, optionally after concentrating said solution, is re-used in step (A) as a cellulose solvent. This process employs an ion exchanger having a cellulose carrier to which groups capable of exchanging ions are attached.

In a preferred embodiment of the process according to the invention, carrier groups are provided which are capable of exchanging anions, particularly tertiary amino groups and/or quaternary ammonium groups.

In another preferred embodiment of the process according to the invention, carrier groups are provided which are capable of exchanging cations, particularly sulfonic acid groups and/or carboxylic groups.

The invention further relates to the use of cellulose functionalized with groups capable of exchanging ions for purifying an aqueous solution of a tertiary amine-oxide, particularly a precipitation bath containing N-methylmorpholine-N-oxide as the tertiary amine-oxide.

Surprisingly, it has been shown that cellulose materials, which are already known to provide excellent purification result when used as carriers in ion exchangers, may be employed to advantage in the amine-oxide process. Specifically, it has been discovered that the cellulose materials may be regenerated in a single-step process. Cellulose is also advantageous because it is a biodegradable polymer.

As mentioned before, cellulose is a known carrier material for carrying ion exchange groups. In "Die chemische Behandlung und Modifizierung der Zellulose" (Rogowin und Galbraich; Georg Thieme Verlag, 1983), starting at page 97 there are references to the use of modified cellulose in ion exchangers. Celluloses modified with carboxylic and sulfo groups for use in cation exchangers and celluloses modified with polyvinylpyridine for use in anion exchangers are described. Furthermore, the use of these anion exchangers as a filter material for universal gas masks or for discoloring agar-agar solutions in combination with cation exchangers is disclosed.

The beneficial purifying effect of cellulose materials in the amine-oxide process is surprising because the spent NMMO solution contains a number of different chemical substances whose chemical behavior has not yet been clarified in detail. Furthermore it could not have been expected that the ion exchangers used in the present invention, in contrast to the styrene-divinylbenzene copolymerizates proposed in the art as ion-exchangers for the amine-oxide process, may be regenerated completely after their use in a single-step process because no irreversible coloring occurs. Accordingly a second purification step with a strong acid, as suggested by WO93/11287, is not necessary. Even purification with other agents (e.g. volatile organic acids), is not necessary.

Furthermore it has been found that the absorbing capacity of the cellulose materials used according to the invention is similar to that of conventional materials (e.g. of a styrene-divinylbenzene copolymerizate).

The invention will now be explained in more detail by the following Examples.

BRIEF DESCRIPTION OF THE PREFERRED EMBODIMENTS (A) Preparation of a cellulose material having quaternary ammonium groups as functional groups Cellulose (27 g, "Viscokraft" sieve fraction <100 μm), (3-Chloro-2-hydroxy)-N,N,N-trimethylpropane-ammoniumchloride (55.1 g, DEGUSSA, active content 57%), NaOH (13.36 g) and 150 ml of water were mixed and stirred for 24 hours. Then the mixture was neutralized with 1% HCl, filtrated, the residue was washed with water and dried in the drying chamber at 50° C.

(B) Determination of the capacity of the modified cellulose when used as an anion exchanger 5 g of the modified cellulose produced in (A) were charged with an aqueous salty solution containing 20% NMMO. 10 ml fractions of each were collected and their ion concentrations were determined. The difference between the absolute ion amounts of the supply per fraction and the amounts in the eluate per fraction gives the amount adsorbed on the modified cellulose. All values in Tables 1 and 2 are expressed in mg/l, with the exception of "fraction cumulated", which is expressed in ml.

The NMMO solution used for charging had the following salt content,

TABLE 1

| Formiate | Cl$^-$ | NO$_2^-$ | NO$_3^-$ | SO$_4^{2-}$ | Oxalate |
|---|---|---|---|---|---|
| 80 | 131 | 29 | 31 | 8100 | 59 |

In each of the fractions of the eluate, the following ion concentrations were determined:

TABLE 2

| Fractions cumulated | Formiate | Cl$^-$ | NO$_2^-$ | NO$_3^-$ | SO$_4^{2-}$ | Oxalate |
|---|---|---|---|---|---|---|
| 10 | 0.9 | 0.6 | 0.5 | 0.5 | 3 | 0 |
| 20 | 2.7 | 3.5 | 0.5 | 1 | 168 | 1 |
| 30 | 16 | 18 | 2 | 5 | 1180 | 8 |
| 40 | 70 | 86 | 8 | 27 | 5725 | 38 |
| 50 | 87 | 112 | 11 | 41 | 7422 | 50 |
| 60 | 89 | 116 | 12 | 44 | 7852 | 54 |
| 70 | 89 | 120 | 12 | 47 | 8120 | 57 |
| 80 | 91 | 121 | 12 | 48 | 8415 | 59 |
| 90 | 90 | 122 | 13 | 49 | 8604 | 62 |
| 100 | 93 | 124 | 12 | 49 | 8681 | 63 |

From the total of the separated components, the capacity of the modified cellulose as an ion exchanger may be calculated as 1,088 milliequivalent/g of cellulose.

(C) Discoloring 5 g of the modified cellulose prepared in (A) was slurried in water, packed into a chromatographic column and converted into the OH$^-$ form with 20 ml of 0.5% NaOH. Then a total of 100 ml of spent, colored (extinction at 470 nm: 2.52) aqueous NMMO solution, which was obtained from a precipitation bath used in the production of cellulose fibers according to the amine-oxide process, was added in portions to the column. The extinction of the eluate was measured in fractions of 10 ml each at a wavelength of 470 nm. The results are given in Table 3.

TABLE 3

| (Charging) | | | |
|---|---|---|---|
| Eluate (ml; cumulated) | extinction of the eluate | Eluate (ml; cumulated) | extinction of the eluate |
| 10 | 0.00246 | 80 | 0.2140 |
| 20 | 0.0050 | 90 | 0.3016 |
| 30 | 0.0219 | 100 | 0.5173 |
| 40 | 0.0543 | | |
| 50 | 0.0897 | | |
| 60 | 0.1203 | | |
| 70 | 0.1953 | | |

From Table 3 it can be seen that a significant increase of the extinction can be observed only after adding a total of 90 ml of colored NMMO solution. Thus, the modified cellulose is highly suited for discoloring the NNMO solution.

After adding the NMMO solution, the charged, modified cellulose was regenerated with aqueous NaOH and the extinction of the eluate was measured again, 30 ml of eluate was collected for the first measurement, 20 ml for the second measurement and an additional 30 ml was collected for each of the third and fourth measurements. The results for this regeneration experiment are indicated in Table 4.

TABLE 4

| (Regeneration) | |
|---|---|
| Eluate (ml; cumulated) | Extinction of the eluate |
| 30 ml | 0.7828 |
| 50 ml | 13.5 |
| 80 ml | 0.4215 |
| 110 ml | 0.01153 |

Table 4 shows that after a total of 110 ml of eluate is obtained, practically no discoloring of the eluate is observed. Furthermore, the material of the ion exchanger (i.e. the modified cellulose) was not discolored. Therefore it is possible to remove the attached colorants from the ion exchanger (i.e. the modified cellulose) merely by regeneration with NaOH, thereby preparing the ion exchanger to be used in a next purification cycle. This result is an improvement over known processes which could not achieve this result.

Regeneration may be carried out using alcohols (e.g. ethanol) instead of aqueous NaOH.

We claim:

1. A process for preparing cellulose molded bodies comprising the steps of:
    (a) dissolving cellulose in an aqueous solution of a tertiary amine oxide to produce a moldable cellulose solution,
    (b) molding said cellulose solution,
    (c) conducting said molded cellulose solution into an aqueous precipitation bath, thereby precipitating a cellulose molded body and contaminating the precipitation bath,
    (d) purifying said contaminated precipitation bath by contacting said contaminated precipitation bath with an ion exchanger, said ion exchanger comprising a cellulose carrier having attached ion exchange groups, thereby producing a purified precipitation bath.

2. A process according to claim 1 wherein the tertiary amine oxide is N-methylmorpholine-N-oxide.

3. A process for preparing cellulose molded bodies according to claim 1 further comprising the step of concentrating said purified precipitation bath and dissolving cellulose therein in step (a).

4. A process according to claim 1 wherein the ion exchange groups are anion exchange groups.

5. A process according to claim 4 wherein the anion exchange groups are selected from the group consisting of tertiary amine groups, quaternary ammonium groups and combinations thereof.

6. A process according to claim 1 wherein the ion exchange groups are cation exchange groups.

7. A process according to claim 6 wherein the cation exchange groups are selected from the group consisting of sulfonic acid groups, carboxylic groups and combinations thereof.

8. A process according to claim 1 wherein the ion exchange groups are selected from the group consisting of tertiary amine groups, quaternary amine groups, sulfonic acid groups and combinations thereof.

9. A process according to claim 1 further comprising regenerating the ion exchanger in a single step process.

10. A process for purifying an aqueous solution of a tertiary amine oxide comprising contacting the solution with an ion exchanger, said ion exchanger comprising a cellulose carrier having attached ion exchange groups.

11. Process according to claim 10 wherein the tertiary amine oxide is N-methylmorpholine-N-oxide.

* * * * *

UNITED STATES PATENT AND TRADEMARK OFFICE
CERTIFICATE OF CORRECTION

PATENT NO. : 5,602,247

DATED : February 11, 1997

INVENTOR(S) : Eduard Mulleder and Henrich Firgo

It is certified that error appears in the above-indentified patent and that said Letters Patent is hereby corrected as shown below:

Col. 2, line 31, "copolymefizate" should read --copolymerizate--

Col. 2, line 64, "NNMO" should read --NMMO--

Col. 5, line 17, "NNMO" should read --NMMO--

Signed and Sealed this

Third Day of June, 1997

Attest:

BRUCE LEHMAN

Attesting Officer

Commissioner of Patents and Trademarks